United States Patent
Knepshield et al.

[11] Patent Number: 5,545,172
[45] Date of Patent: Aug. 13, 1996

[54] ROCKING FOOT PLATE FOR SURGICAL KNIFE

[75] Inventors: William R. Knepshield, Malvern; Kristen K. Fay, Glen Mills; William Knepshield, Jr., West Chester, all of Pa.

[73] Assignee: Malvern Technologies, Inc., Malvern, Pa.

[21] Appl. No.: 255,035

[22] Filed: Jun. 7, 1994

[51] Int. Cl.⁶ .................................. A61B 17/32
[52] U.S. Cl. .................... 606/166; 606/167; 30/293
[58] Field of Search .................... 606/166, 167, 606/172; 30/293, 289, 290, 368, 310

[56] References Cited

U.S. PATENT DOCUMENTS

| 3,085,330 | 4/1963 | Lewinski et al. | 30/293 |
| 3,178,817 | 4/1965 | Rubinstein | 30/293 |
| 4,473,076 | 9/1984 | Williams et al. | 606/172 |
| 4,569,133 | 2/1986 | Schmidt | 606/172 |

FOREIGN PATENT DOCUMENTS

| 2113550 | 8/1983 | United Kingdom | 606/167 |

*Primary Examiner*—Gary Jackson
*Assistant Examiner*—William W. Lewis
*Attorney, Agent, or Firm*—Duane, Morris & Heckscher

[57] ABSTRACT

This invention discloses a surgical knife which is suitable for use in astigmatic radial keratotomy, and similar procedures and which includes an elongated diamond blade, a blade holder, and a rocking foot plate means pivotally attached to the knife body, and a method of performing a radial keratotomy procedure utilizing such a knife. Said rocking foot plate means has a lower surface for contacting and rocking over a peripheral portion of corneal tissue during a keratorefractive incision. The ability of the foot plate to rock assists surgeons in more precisely controlling blade movement during delicate surgeries, such as radial keratotomy.

17 Claims, 5 Drawing Sheets

ROCKING FOOT PLATE FOR SURGICAL KNIFE

FIELD OF THE INVENTION

This invention relates to a surgical knife suitable for use in surgical procedures requiring depth control or precise positioning, including radial keratotomy, astigmatic keratotomy, intraocular lens implantation, and the like. More specifically, this invention relates to a surgical knife which includes an elongated diamond blade, a blade holder, and a rocking foot plate means pivotally attached to the knife body. This invention also relates to a method of performing radial keratotomy procedures utilizing such a knife.

BACKGROUND OF THE INVENTION

Myopic patients can now undergo radial keratotomy procedures in order to achieve refractive correction. During these keratorefractive procedures, surgeons reconfigure the myopic patient's cornea so that the light entering the eye focuses more accurately on the retina. Surgical knives which make precise radial incisions in the cornea assist the surgeons in performing this reconfiguration.

The goal of both the surgeon and the patient during a radial keratotomy procedure is to achieve refractive correction. This goal has not always been reached, however, because of the many potential problems which a surgeon may encounter. One danger of the procedure involves an undesired invasion of the central optical zone, caused by slight irregular movements of the patient's eye or the surgeon's hand. Incisions invading the superficial layers of the optical zone are associated with optical glare, since the resulting surface scarring has a different refractive index than the surrounding corneal tissue. Another potential problem involves the risk of puncturing the cornea during the incision process. Such a puncture could create an entrance for bacteria to enter the anterior chamber of the eye, with the attendant risks of infection and complications.

In order to minimize the above described problems, surgical knives have been designed with special features. One such special feature is the foot portion, one or more feet attached to the blade holder which frame the distal end of the blade. The foot portion helps surgeons monitor the incision making process by controlling incision depth. The foot portion acts as a limit to incision depth, since the knife blade must stop penetrating the corneal tissue when the foot portion comes in contact with such tissue. In this way, the foot portion assists the surgeon in controlling the depth of the incisions.

Modern foot plates for radial keratotomy knives have been known to assume an "American," "Russian," or "Universal" configuration. The American foot plate generally has a small contact surface at its distal end and an oblique angled surface for permitting the oblique cutting edge of an American-style diamond knife to reveal its cutting edge. The Russian foot portion is designed with a larger surface for contacting the cornea and exhibits a right-angle configuration. Since Russian cutting edges are substantially vertical, the Russian feet do not exhibit an oblique surface. More recently, a Universal foot portion which exhibits properties of the American and Russian feet has been developed for combined incision blades. The Universal foot portion is more open than an American foot portion for permitting greater visibility of the blade, but it retains a small contact surface.

Although the purpose of the foot portion is to aid surgeons in controlling the precise nature of the incisions, some of the designs of the currently available foot portions have hindered this requisite precision. Many foot portions of currently available surgical knives are attached to the knife body in a fixed position. The blade and foot plate of these knives move over the corneal tissue together as the blade is used to make the incision. Although the foot plate is designed to slide over the tissue, this movement is not always smooth, and provides a source of friction, which can disrupt the motion of the knife blade penetrating the corneal tissue. This inability of the knife blade to move independently of the foot portion has thus hindered the success rate of keratorefractive surgery, since any disruption of free movement which is experienced by the foot portion will necessarily affect the incision.

The contact between the fixed foot plate and the corneal tissue can also lead to a tissue bulge in the area around foot plate contact. When the fixed foot plate exerts pressure on the portion of the corneal tissue over which it slides, the surrounding tissue responds to this pressure by bulging upward, away from the plane of the incision. This tissue bulging is disadvantageous to surgeons, as it interferes with the precision required for the radial incisions.

Accordingly, there is a present need for foot portions that move independently from the knife blade and do not cause tissue bulging. There is also a need to permit greater visibility of the knife blade during surgery while still allowing the blade to move freely through the cornea during incisions. Such a foot portion, to be effective, must still act as a limit to incision depth and length.

SUMMARY OF THE INVENTION

The present invention provides a surgical knife suitable for use in detailed surgical procedures requiring depth control or precise positioning, including radial and astigmatic keratotomy, intraocular lens implantation, and the like. The present invention also provides a method of performing these surgical procedures utilizing such a knife. The knife of this invention includes an elongated diamond blade, a blade holder, and a rocking foot plate pivotally attached to the blade holder. The rocking foot plate includes at least one foot portion, and has a lower surface for contacting and rocking over a peripheral portion of a patient's corneal tissue during a keratorefractive incision. The rocking foot plate helps to control the length and depth of radial incisions made during delicate surgical procedures.

The present invention overcomes the disadvantages of the prior art by providing a surgical knife which includes a foot portion that can move independently from the knife blade. This independence of movement is possible because the foot portion is pivotally attached to the blade holder, thus allowing the foot plate to rock over the corneal tissue while the blade freely makes the incision. The design of this invention allows the blade to make the corneal incision with reduced friction between the foot plate and the tissue to be incised, because the foot plate no longer slides over the corneal tissue, but rocks over it. The present invention thus allows for precise radial incisions by reducing the friction between the foot plate and corneal tissue, while still providing the requisite barrier for incision depth control.

The rocking foot plate means of this invention provides another benefit over the prior art, in that this particular configuration allows for better visibility of the tissue being incised, especially when one foot portion is used. Since the foot portion moves independently of the blade and does not slide over the corneal tissue as the blade is used to make the incision, it does not hinder the surgeon's view of the blade or the incision during the procedure. Accordingly, the beginning and end of the incision are visible at all times. Also, this invention allows the diamond blade to be positioned against the rocking footplate for absolute depth control. The surgeon will know the exact position to stop and start incising. This invention provides for precisely "straight" incisions as guided by the rocking foot portions.

The present invention also overcomes the prior art disadvantages of causing the corneal tissue to bulge during the incision process. By rocking over the corneal tissue, the knife of the present invention alleviates corneal tissue bunching or bulging ahead of the incision caused by a sliding foot plate. The lack of tissue bulging in the incision area allows the surgeon to make more accurate incisions by minimizing distortions in the corneal surface.

Prior art foot plate configurations were also known to cause bulging between the feet and knife blade. This type of bulging can be reduced in certain embodiments of this invention where either one or both feet abut, or nearly abut, the knife blade. The closer the blade is to the foot plate, the less chance there will be for the tissue to bulge between the blade and feet.

One preferred embodiment of the foot plate means of the rocking foot portion is an arcuate configuration of constant thickness. In an alternative embodiment, the foot plate means is an arcuate configuration of tapering thickness. The purpose of the varying thickness is incision depth control over the tapering thickness of the cornea. This invention also can employ delimiting mechanisms to help limit the length of the incision, biasing means for helping the rocking foot plate return to a central location, and locking pins to selectively fix the foot plate location.

BRIEF DESCRIPTION OF THE DRAWINGS

The accompanying drawings illustrate preferred embodiments of the invention according the practical applications of the principles thereof, and in which.

DETAILED DESCRIPTION OF THE INVENTION

Figure 1:
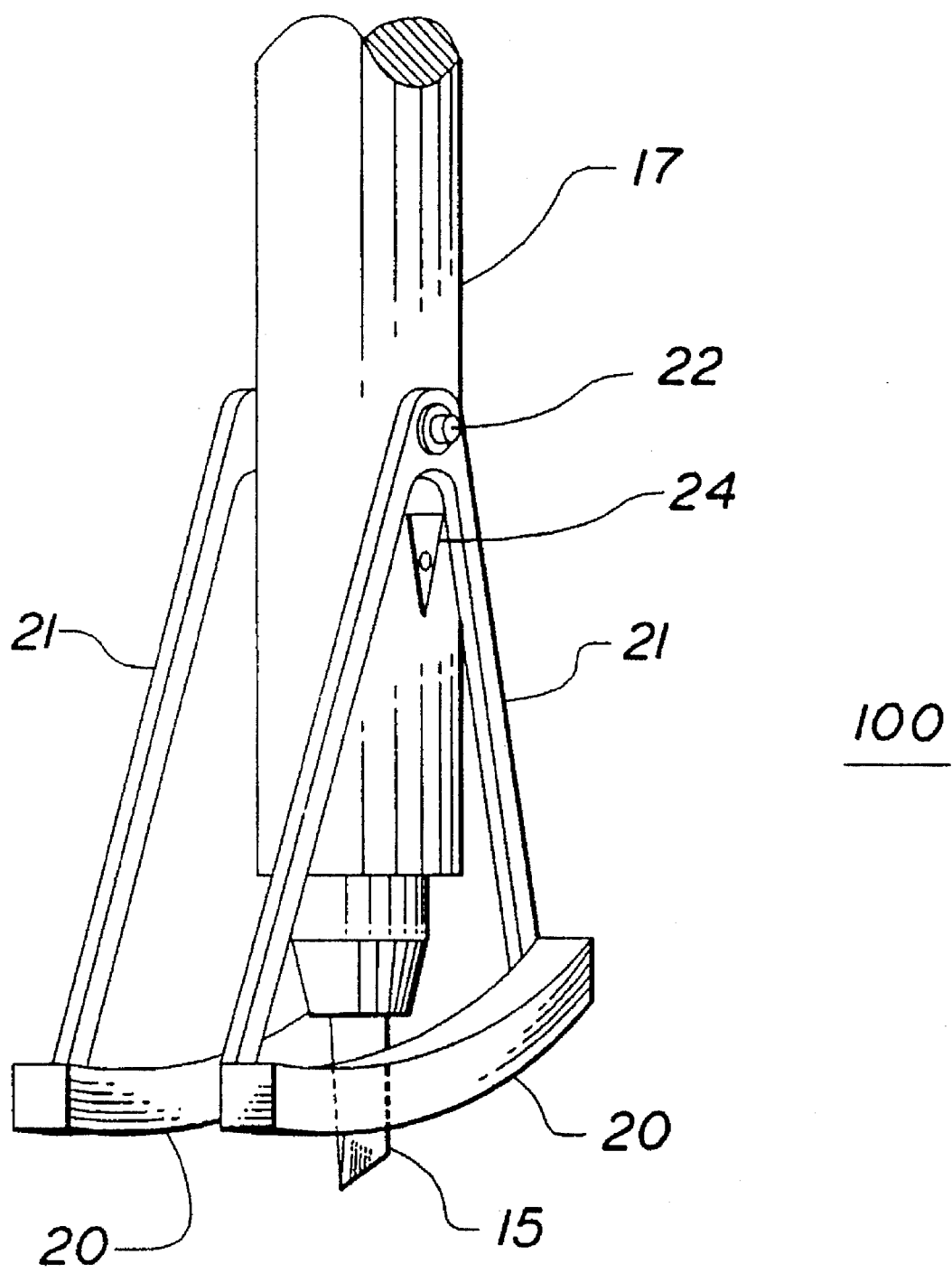
FIG. 1: is a perspective view of a surgical knife, including a rocking foot plate attached to a blade holder by lever arms.

The knives of this invention are suitable for use in surgical procedures requiring depth control and precise positioning, including radial keratotomy, astigmatic keratotomy, intraocular lens implantation, and the like. With reference to the figures and particularly with respect to FIGS. 1–3, there is shown a preferred surgical knife 100 including a knife blade 15. The knife blade is typically constructed of a hard gemstone, such as a diamond, sapphire or ruby. The blade is honed to a sharp cutting edge at its most distal portions. The knife blade 15 is usually mounted by epoxy adhesive or by brazing into a blade holder 17 which is sized to fit comfortably within a surgeon's hand. In an important aspect of this invention, the surgical knife 100 is equipped with rocking foot plate means pivotably attached to the blade holder. In the preferred embodiment shown in FIG. 1, the rocking foot plate means comprises foot plate portions 20 mounted to the blade holder 17 by supporting lever arms 21. Preferably the lever arms are disposed in a pivoting relationship by a pivot connector 22, which can be a screw or rivet.

The preferred foot plate portions 20 are located on opposite lateral sides of the knife blade 15. They include an arcuate lower surface for rotating against the curved surface of a cornea. The blade 15 is set to extend beyond this surface a distance "A", which is typically about 50–750 μ.

Figure 4A:
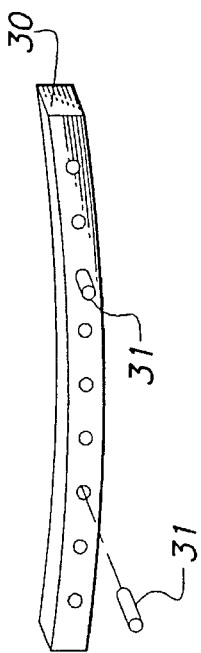
FIG. 4a: is a side perspective view of an alternative foot plate portion having removable delimiting pins.
Figure 4B:
FIG. 4b: is a side perspective view of an alternative foot plate portion having a tapered cross section.
Figure 4C:
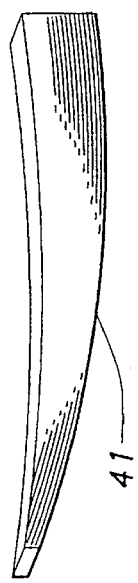

There are many different arrangements which would be suitable for the rocking foot plate portion of this invention. As shown in FIGS. 4a and 4b, the foot plate portions can include delimiting pins 31 which automatically stop the knife blade when a certain length incision is generated. The pins can also be used to connect the ends of a pair of foot plate portions 30 so that they rock in unison during an incision. This cooperative relationship can equally be accomplished by joining, as by soldering or brazing, the lever arms 21 to the pivot connector 22.

As shown in alternative foot plate portion 40 of FIG. 4b, the cross-section can include a taper so as to provide further extension of the knife blade 15 beyond the lower surface of the foot plate portion embodiment 40 when incising thicker peripheral corneal tissue, for example. This taper can be calculated to provide consistent incisions up to 90%–100% of the pachometry readings irrespective of the location in the cornea.

Figure 3:
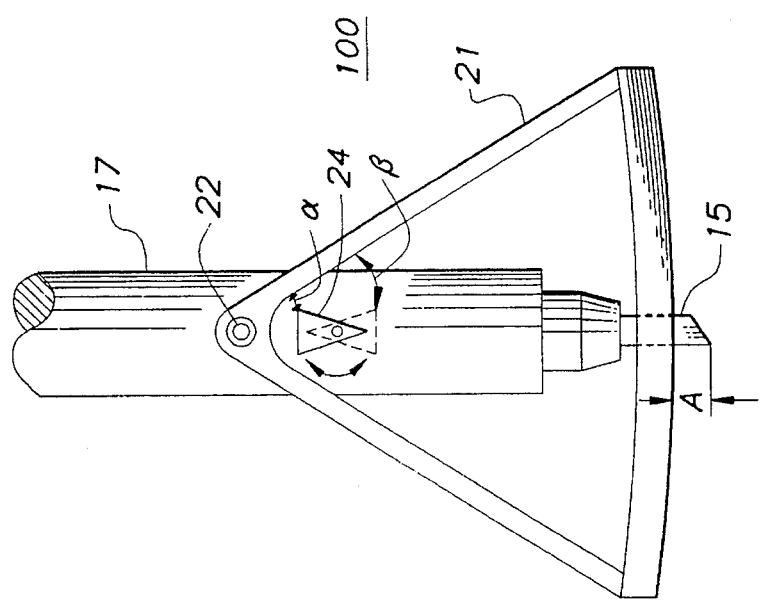
FIG. 3: is a side planar view of the surgical knife of FIG. 1.
Figure 2:
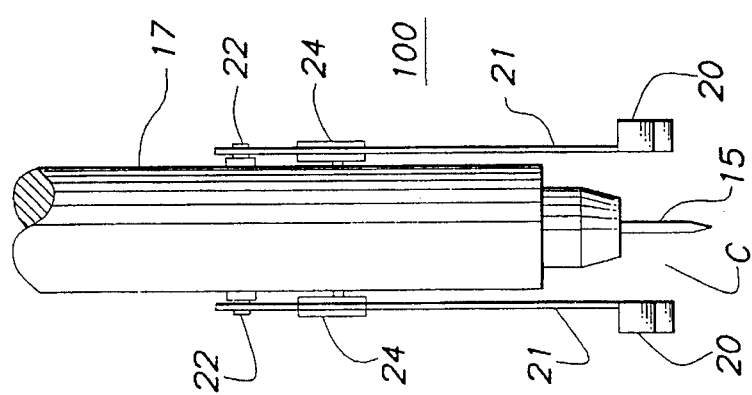
FIG. 2: is a front planar view of the surgical knife of FIG. 1.

As shown clearly in FIGS. 2 and 3, a delimiting mechanism 24 is provided to restrict the rotation of the foot plate portions 20. The delimiting mechanism 24 preferably comprises a ratcheting spacer that defines at least two arcs of rotation for the foot plate portions 20. In FIG. 3, there is described a first arc of rotation α between a corner of the delimiting mechanism 24 and the internal surface of the lever arm 21. When this mechanism 24 is rotated 180°, a new arc of rotation β is formed between a corner of the mechanism and the inner surface of the lever arm 21. Naturally, the delimiting mechanism 24 can include a series of bumps or geometric features that will enable multiple arcs of rotation. The adjustment to the arc of rotation can also be accomplished by mechanical adjustments to the pivot connector 22, or by a series of adjustable pins or rails located along the blade holder which selectively restrict the arc of rotation of the lever arms 21. As indicated above with respect to FIG. 4a, delimiting pins can also be used to restrict the arc of the blade 15 between the foot portions 20.

Figure 6:
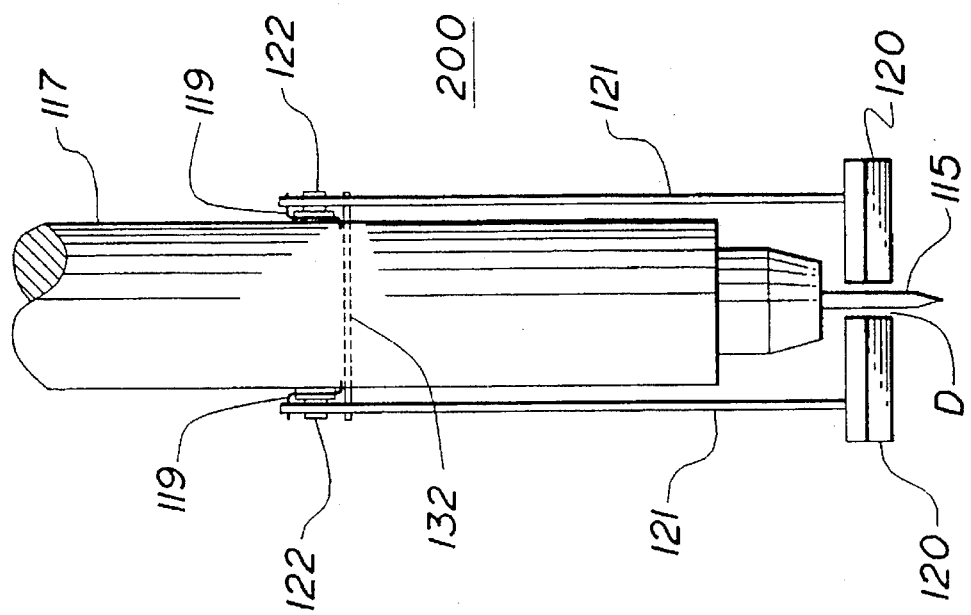
FIG. 6: is a front planar view of the surgical knife of FIG. 5.

The surgical knife of this invention can exhibit a variety of forms. In another preferred embodiment, a knife 200 is provided which includes a knife blade 115 held in place by a blade holder 117. This surgical knife includes lever arms 121 for supporting the foot plate portions 120 and is rotatably connected by pivot connector 122 to the blade holder 117. Unlike surgical knife 100, however, this knife is equipped with three alternative mechanisms or structures targeted to various surgical needs. As described further in FIG. 6, the foot plate portions 120 are extended to abut, or nearly abut as measured by distance "D", the knife blade 115. The distance "D" is preferably less than about 1 mm, more preferably less than about 0.1 mm. In this way, bulging between the knife blade 115 and the inside surface of the foot plate portions 120 can be minimized or avoided entirely. This is important since such bulges can interfere with the surgical procedure and produce unreliable angles and depths to the incision.

The surgical knife embodiment 200 also is equipped with adjustable locking pins 132 which can be located through the lever arms 121 and into the blade holder 117. In this way, the foot plate portions 120 can be locked into any number of set positions upon demand.

Figure 5:
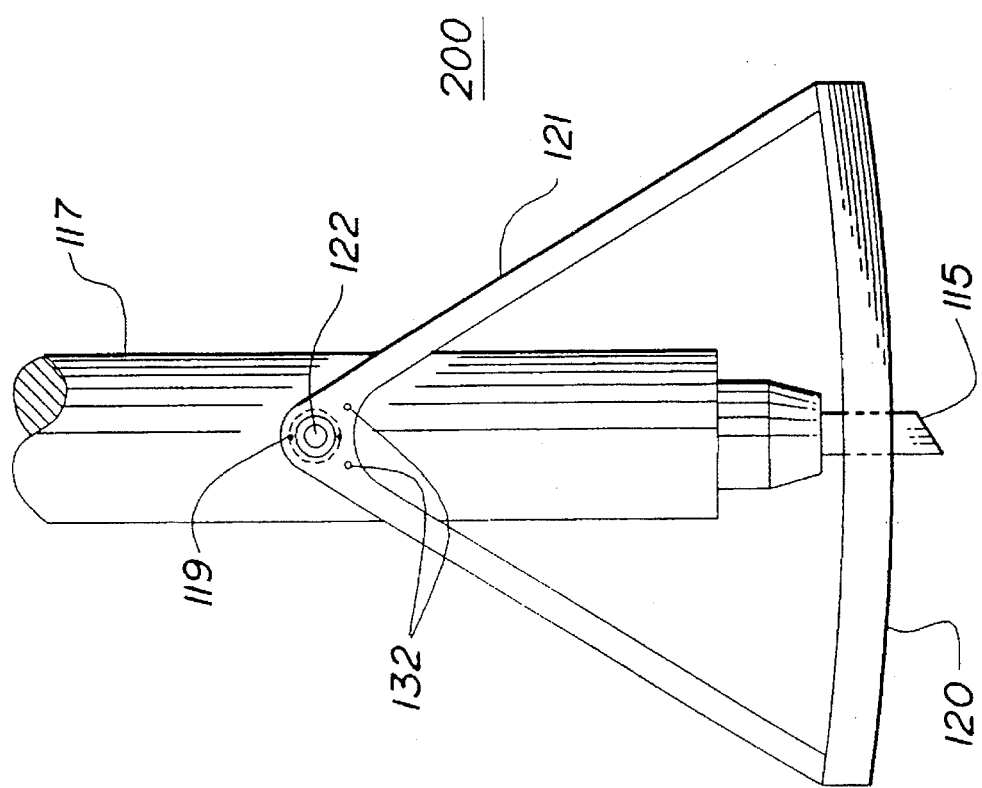
FIG. 5: is a side planar view of an alternative surgical knife of this invention disclosing a bias spring and locking pins.

This surgical knife 200 is also equipped with a bias spring 119 which helps to restore the foot plate portions 120 to a central position about the knife blade 115, as shown in FIG. 5. The bias springs 119 are shown for example purposes only, and this feature can be accomplished by any resilient structure, such as a resilient washer etc., located either internally or externally from the blade holder 117.

Figure 7:
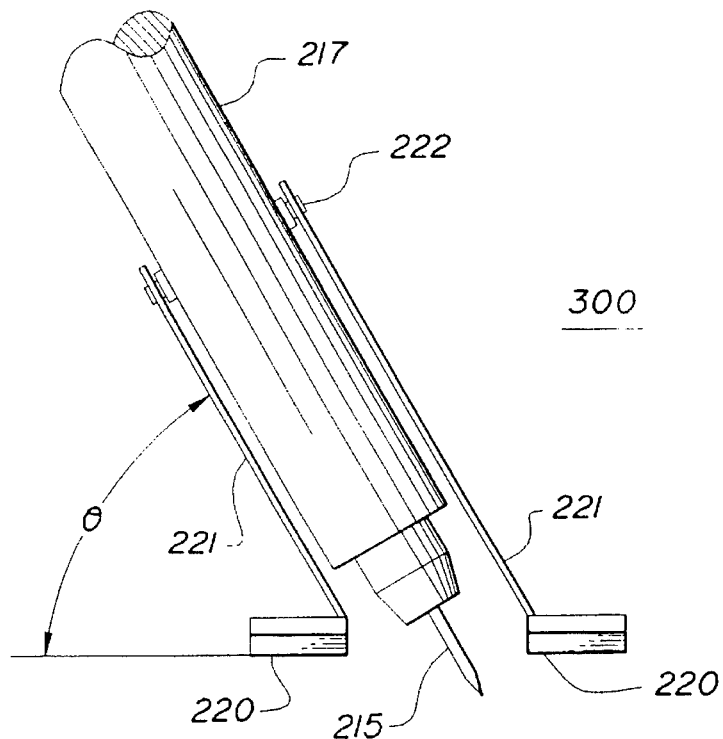
FIG. 7: is a front planar view of an alternative embodiment surgical knife which is tilted at an angle from the corneal surface.
Figure 8:
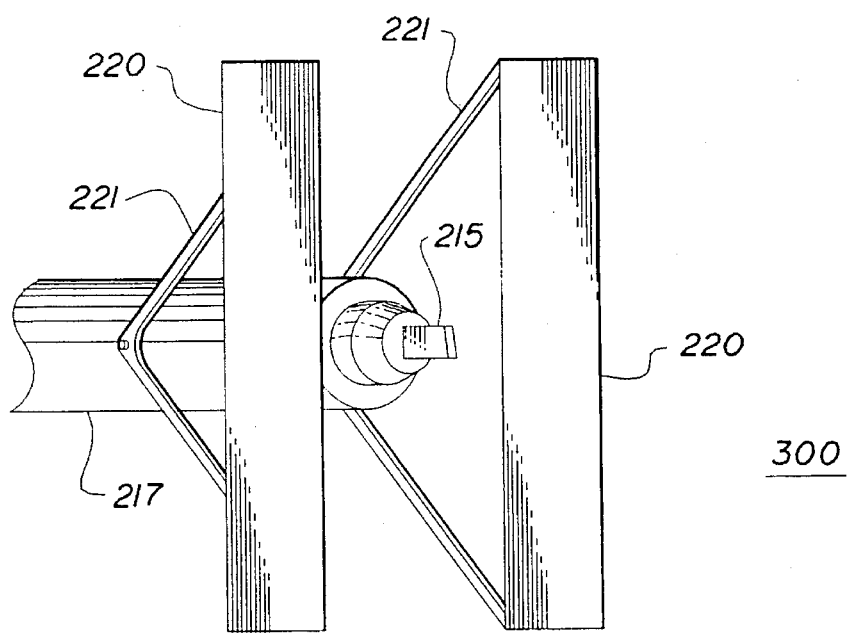
FIG. 8: is a bottom perspective view of the surgical knife embodiment of FIG. 7.

Another alternative embodiment of this invention is described by the surgical knife 300 found in FIGS. 7 and 8. In this configuration, one or more foot plate portions 220 are inclined by an angle "θ" with respect to the plane of the cornea. (It is understood that the "plane of the cornea" is actually a plane containing the tangent drawn at a desired incision point along the curved corneal surface.) This can be accomplished by merely bending the lever arms 221 with respect to the foot plate portions 220. Since this feature should not effect the rotation about the pivot connector 222, the foot plate portions 220 are free to rotate. The lever arms 221 can be mounted to the blade holder 217 in the same manner as described for previous embodiments. This embodiment is particularly helpful in making lenticular cuts in the cornea. It may also be helpful to provide the foot plate portions 220 with a curvature in the plane of the cornea so as to create an arcuate incision.

Figure 9:
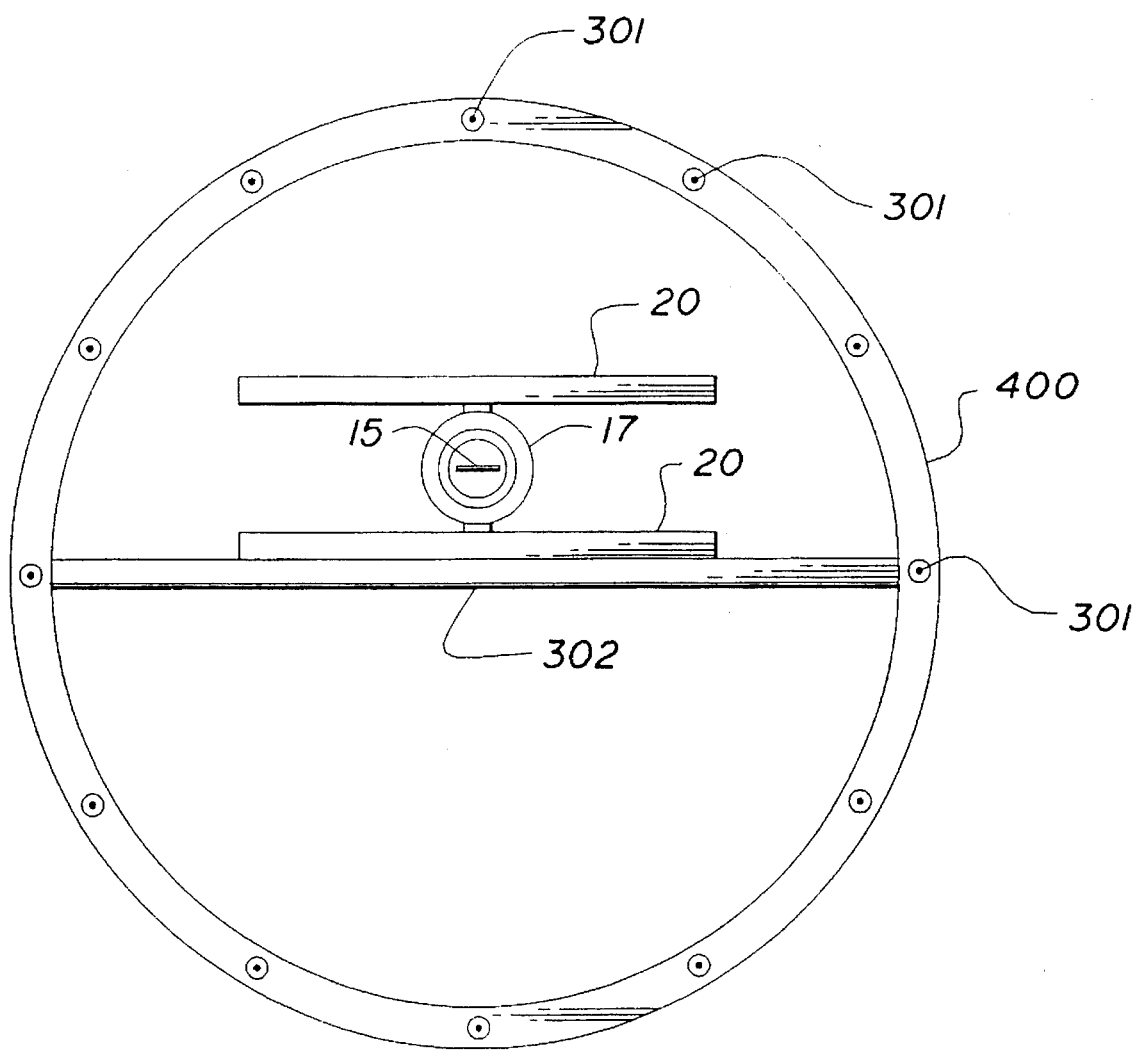
FIG. 9: is a bottom view of the knife of FIG. 1 being used in connection with a globe fixation device.

An alternative system used for the surgical knives of this invention is depicted in FIG. 9. In this surgical method, the knife 100 is used in conjunction with a globe fixation device 400 which holds the eye in place during the surgery through a series of small pins 301. (Equivalent vacuum assisted means could also be employed.) The fixation device support bar 302 can be used as a brace against which the foot portions 20 travel. When an incision is made in a radial direction, the foot portion 20 is braced against the globe fixation device 400, so that the knife blade cannot experience any undesired movement in the lateral direction. Naturally, the globe fixation device 400 can be equipped with support bands in various locations which lend themselves more directly to radial keratotomy wound placement.

The length, thickness and shape of the foot plate portions of this invention can be varied greatly in order to accommodate various types of surgery, preferences and techniques. They are preferably constructed using a lightweight, non-corrosive material such as plastic, stainless steel or titanium. They can include a textured surface, to hold the cornea in position during the incision making process. The textured surface can grip onto the cornea, so that the cornea will not move while the blade is used to make the incision. Such a surface can be created by etching the lower surface of the feet, by applying coatings of materials, such as carborundum, diamond or silicon carbide, or tungsten carbide to the lower surface of the feet, or by mechanical working, such as machining, grinding or bead blasting, for example.

The surgical knives of this invention can be used in various micro-surgical procedures, and especially radial keratotomy procedures. To perform a radial keratotomy procedure using the surgical knives of this invention, the elongated knife blade 15 extending from the rocking foot plate portions 20 is first pierced into the corneal tissue. A radial incision is then made in the tissue in either a "downhill" centrifugal, or an "uphill" centripetal direction. Of course, combination surgical techniques can be used with the foot plates of this invention for providing both centrifugal and centripetal cuts within the same incision. During these procedures, the lower portion of the foot plate contacts and rocks over the curved surface of the cornea in order to control the incision depth first, in a downhill direction, and then, in an uphill direction.

The knife blade 15 can fairly move through the corneal tissue in clear view of the surgeon while making these incisions, since the foot plate portions 20 can rock independently from the movement of the knife blade 15. This eliminates the obstructed view that typically occurs with standard Russian or American foot plate constructions. The delimiting mechanism 24 can be set to achieve incision lengths between any two points in the corneal quadrants, including between central, mid-central, mid, mid-peripheral and peripheral locations. The foot portions can also include markings or notches for providing a measure of incision length, for example, in millimeters.

From the foregoing, it can be realized that this invention provides improved keratotomy knives and procedures for providing greater control of incision depth and direction. Although specific knives and procedures are disclosed, this invention would also be suitable for any surgical or a microsurgical application, including orthopedic microsurgery and neurosurgery. Although various embodiments of a surgical knife design have been illustrated, this is for the purpose of describing, but not limiting the invention. Various modifications, which will become apparent to one skilled in the art, are also within the scope of this invention described in the attached claims.

LIST OF REFERENCE NUMERALS 15 knife blade
17 blade holder
20 foot plate portions
21 lever arms
22 pivot connector
24 delimiting mechanism
30 alternative foot plate portion
31 delimiting pins
40 tapered foot plate portion alternative
100 surgical knife
115 knife blade
117 blade holder
119 bias spring
120 foot plate portions
121 lever arms
122 pivot connector
132 locking pins
200 surgical knife
215 knife blade
217 blade holder
220 foot plate portions
221 lever arms
222 pivot connector 300 surgical knife
301 pins
302 support band
400 globe fixation device

What is claimed is:

1. A surgical knife for making radial keratotomy incisions in a cornea, comprising:
   (a) an elongated diamond blade having at least one cutting surface capable of making said incisions;
   (b) a blade holder for securing said blade at a distal portion of said blade holder, said blade holder sized to fit into a surgeon's hand; and
   (c) rocking foot plate means pivotally attached to said blade holder, said foot plate means having an upper and lower surface, said lower surface contacting and rocking over a superficial portion of the cornea during said incisions.

2. The surgical knife of claim 1, further comprising delimiting means located on said blade holder for selectively limiting a rotation of said rocking foot plate means.

3. The surgical knife of claim 2, wherein said delimiting means comprises a ratcheting spacer rotatably mounted to said blade holder, said spacer providing at least two different arcs of rotation for said foot plate means by rotating from a first to a second position on said blade holder.

4. The surgical knife of claim 1, wherein said rocking foot plate means comprises a pair of substantially parallel foot plate portions disposed laterally along the sides of said blade.

5. The surgical knife of claim 4, wherein each of said foot plate portions is attached separately to the blade holder by a pair of lever arms.

6. The surgical knife of claim 5, wherein said foot plate portions are linked together by a lateral pin disposed therebetween to rotate said foot plate portions in unison.

7. The surgical knife of claim 4, wherein each of said foot plate portions is disposed within about 1 mm from a lateral side of said blade to minimize bulging of corneal tissue between said blade and foot plate portions.

8. The surgical knife of claim 4, further comprising a spring member attached to connect said blade holder and said foot plate portions for biasing said foot plate portions.

9. The surgical knife of claim 4, wherein each of said foot plate portions is disposed to swing in an arc around a distal end of said knife body.

10. The surgical knife of claim 4, wherein said foot plate portions comprise upper and lower arcuate surfaces.

11. The surgical knife of claim 10, wherein said foot plate portions comprise a constant thickness between said upper and lower surfaces.

12. The surgical knife of claim 10, wherein said foot plate portions comprise a tapering thickness between said upper and lower surfaces.

13. The surgical knife of claim 4, wherein said foot plate portions comprise a curved portion in a horizontal plane.

14. The surgical knife of claim 4, wherein the lower surface of each foot plate portion comprises a textured surface.

15. A radial keratotomy knife, comprising:
   (a) an elongated diamond blade having a first cutting edge thereon;
   (b) a blade holder for retaining said diamond blade; and
   (c) a pair of rocking foot portions located at a distal end of said blade holder being pivotally mounted to said blade holder so as to swing about a distal portion of said diamond blade during a radial keratotomy procedure.

16. A method of performing a radial keratotomy procedure for correcting a refractive error in the focusing of light through a cornea, comprising;
   (a) providing a surgical knife including an elongated diamond blade having at least one cutting surface thereon, a blade holder for securing said blade, and a rocking foot plate means pivotally attached to said blade holder for contacting and rocking over a superficial layer of the cornea during an incision, said cutting surface extending beyond a distal side of said foot plate means;
   (b) piercing into said cornea with said blade to form an incision while resting said distal side of said foot plate means against a curved surface portion of said cornea; and
   (c) rotating said foot plate means along the curved surface of the cornea whereby the depth of said incision is controlled.

17. The method of claim 16, wherein said foot plate means minimizes a bulging error by pressing on said cornea.

* * * * *